US 12,369,800 B2

United States Patent
Li et al.

(10) Patent No.: US 12,369,800 B2
(45) Date of Patent: *Jul. 29, 2025

(54) METHODS FOR ASSESSING A VESSEL WITH SEQUENTIAL PHYSIOLOGICAL MEASUREMENTS

(71) Applicant: BOSTON SCIENTIFIC SCIMED, INC., Maple Grove, MN (US)

(72) Inventors: Wenguang Li, Los Gatos, CA (US); Qian Li, San Jose, CA (US); Justin Michael Lerman, Monte Sereno, CA (US); David Burgess, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 682 days.

This patent is subject to a terminal disclaimer.

(21) Appl. No.: 17/702,213

(22) Filed: Mar. 23, 2022

(65) Prior Publication Data

US 2022/0211281 A1 Jul. 7, 2022

Related U.S. Application Data

(63) Continuation of application No. 16/283,235, filed on Feb. 22, 2019, now Pat. No. 11,311,196.

(Continued)

(51) Int. Cl.
*A61B 5/02* (2006.01)
*A61B 5/00* (2006.01)
(Continued)

(52) U.S. Cl.
CPC .......... *A61B 5/02007* (2013.01); *A61B 5/021* (2013.01); *A61B 5/02158* (2013.01);
(Continued)

(58) Field of Classification Search
None
See application file for complete search history.

(56) References Cited

U.S. PATENT DOCUMENTS

| 3,273,447 A | 9/1966 | Wallace |
| 3,963,323 A | 6/1976 | Arnold |

(Continued)

FOREIGN PATENT DOCUMENTS

| CN | 102469943 A | 5/2012 |
| DE | 202014100938 U1 | 3/2014 |

(Continued)

OTHER PUBLICATIONS

International Search Report and Written Opinion dated May 29, 2017 for International Application No. PCT/US2017/018905.

(Continued)

*Primary Examiner* — Michael R Bloch
(74) *Attorney, Agent, or Firm* — Seager, Tufte & Wickhem, LLP

(57) ABSTRACT

A method, device, and system for evaluating a vessel of a patient, and in particular the hemodynamic impact of a stenosis within the vessel of a patient. Proximal and distal pressure measurements are made using first and second instrument while the first instrument is moved longitudinally through the vessel from a first position to a second position and the second instrument remains in a fixed longitudinal position within the vessel. A series of pressure ratio values are calculated, and a pressure ratio curve is generated. One or more stepped change in the pressure ratio curve are then identified and/or located using an Automatic Step Detection (ASD) process and/or algorithm. The ASD includes identifying a general position of a starting point of the stepped change by identifying a change in the pressure ratio values within a first window along the pressure ratio curve that is at or above a first threshold change value, and identifying an (Continued)

optimized position of the starting point by identifying a change in the pressure ratio values within a second window along the pressure ratio curve that is at or above a second threshold change value, wherein the second window is smaller than the first window, and the second threshold change value is smaller than the first threshold change value.

20 Claims, 5 Drawing Sheets

Related U.S. Application Data

(60) Provisional application No. 62/634,501, filed on Feb. 23, 2018.

(51) Int. Cl.
*A61B 5/021* (2006.01)
*A61B 5/0215* (2006.01)
*A61B 5/026* (2006.01)
*A61B 5/107* (2006.01)

(52) U.S. Cl.
CPC ............ *A61B 5/489* (2013.01); *A61B 5/7235* (2013.01); *A61B 5/742* (2013.01); *A61B 5/026* (2013.01); *A61B 5/1076* (2013.01); *A61B 2562/0247* (2013.01)

(56) References Cited

U.S. PATENT DOCUMENTS

| | | |
|---|---|---|
| 4,112,941 A | 9/1978 | Larimore |
| 4,487,206 A | 12/1984 | Aagard |
| 4,711,246 A | 12/1987 | Alderson |
| 4,771,782 A | 9/1988 | Millar |
| 4,893,630 A | 1/1990 | Roberts, Jr. |
| 4,953,553 A | 9/1990 | Tremulis |
| 5,005,584 A | 4/1991 | Little |
| 5,106,455 A | 4/1992 | Jacobsen et al. |
| 5,135,503 A | 8/1992 | Abrams |
| 5,178,159 A | 1/1993 | Christian |
| 5,238,004 A | 8/1993 | Sahatjian et al. |
| 5,280,786 A | 1/1994 | Wlodarczyk |
| 5,313,957 A | 5/1994 | Little |
| 5,322,064 A | 6/1994 | Lundquist |
| 5,414,507 A | 5/1995 | Herman |
| 5,421,195 A | 6/1995 | Wlodarczyk |
| 5,422,969 A | 6/1995 | Eno |
| 5,425,371 A | 6/1995 | Mischenko |
| 5,427,114 A | 6/1995 | Colliver et al. |
| 5,437,288 A | 8/1995 | Schwartz |
| 5,438,873 A | 8/1995 | Wlodarczyk et al. |
| 5,450,853 A | 9/1995 | Hastings |
| 5,573,520 A | 11/1996 | Schwartz et al. |
| 5,633,963 A | 5/1997 | Rickenbach et al. |
| 5,748,819 A | 5/1998 | Szentesi et al. |
| 5,755,668 A | 5/1998 | Itoigawa et al. |
| 5,772,609 A | 6/1998 | Nguyen et al. |
| 5,779,698 A | 7/1998 | Clayman |
| 5,797,856 A | 8/1998 | Frisbie et al. |
| 5,836,885 A | 11/1998 | Schwager |
| 5,865,801 A | 2/1999 | Houser |
| 5,872,879 A | 2/1999 | Hamm |
| 5,873,835 A | 2/1999 | Hastings et al. |
| 5,902,248 A | 5/1999 | Millar et al. |
| 5,916,177 A | 6/1999 | Schwager |
| 5,938,624 A | 8/1999 | Akerfeldt et al. |
| 5,949,929 A | 9/1999 | Hamm |
| 5,964,714 A | 10/1999 | Lafontaine |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,461,301 B2 | 10/2002 | Smith |
| 6,506,313 B1 | 1/2003 | Fetterman et al. |
| 6,508,803 B1 | 1/2003 | Horikawa et al. |
| 6,565,514 B2 | 5/2003 | Svanerudh et al. |
| 6,575,911 B2 | 6/2003 | Schwager |
| 6,579,246 B2 | 6/2003 | Jacobsen et al. |
| 6,579,484 B1 | 6/2003 | Tiernan et al. |
| 6,585,660 B2 | 7/2003 | Dorando et al. |
| 6,589,164 B1 | 7/2003 | Flaherty |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,244,244 B2 | 7/2007 | Racenet et al. |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,491,484 B2 | 7/2013 | Lewis |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,585,613 B2 | 11/2013 | Nagano |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,757,893 B1 | 6/2014 | Isenhour et al. |
| 8,764,683 B2 | 7/2014 | Meller et al. |
| 8,781,193 B2 | 7/2014 | Steinberg et al. |
| 8,855,744 B2 | 10/2014 | Tolkowsky et al. |
| 8,920,870 B2 | 12/2014 | Weber |

(56) References Cited

U.S. PATENT DOCUMENTS

| | | |
|---|---|---|
| 8,936,401 B2 | 1/2015 | Belleville et al. |
| 8,998,823 B2 | 4/2015 | Manstrom et al. |
| 9,010,286 B2 | 4/2015 | Novak |
| RE45,534 E | 6/2015 | Huennekens et al. |
| 9,052,466 B2 | 6/2015 | Belleville et al. |
| 9,095,313 B2 | 8/2015 | Tolkowsky et al. |
| 9,110,255 B2 | 8/2015 | Lin et al. |
| 9,149,230 B2 | 10/2015 | Caron |
| 9,289,137 B2 | 3/2016 | Cor |
| 9,339,348 B2 | 5/2016 | Davies et al. |
| 9,364,153 B2 | 6/2016 | Merritt et al. |
| 9,375,164 B2 | 6/2016 | Tolkowsky et al. |
| 9,629,571 B2 | 4/2017 | Tolkowsky et al. |
| RE46,562 E | 10/2017 | Huennekens et al. |
| 9,855,384 B2 | 1/2018 | Cohen et al. |
| 9,907,527 B2 | 3/2018 | Dascal et al. |
| 9,974,443 B2 | 5/2018 | Merritt et al. |
| 10,076,301 B2 | 9/2018 | Millett et al. |
| 10,098,702 B2 | 10/2018 | Merritt et al. |
| 10,130,310 B2 | 11/2018 | Alpert et al. |
| 2002/0013527 A1 | 1/2002 | Hoek |
| 2003/0031422 A1 | 2/2003 | Inagaki et al. |
| 2003/0069522 A1 | 4/2003 | Jacobsen et al. |
| 2003/0120175 A1 | 6/2003 | Ehr |
| 2003/0159518 A1 | 8/2003 | Sawatari |
| 2004/0006277 A1 | 1/2004 | Langenhove et al. |
| 2004/0073141 A1 | 4/2004 | Hartley et al. |
| 2004/0181174 A2 | 9/2004 | Davis et al. |
| 2004/0258370 A1 | 12/2004 | Bush |
| 2005/0000294 A1 | 1/2005 | Tenerz et al. |
| 2005/0141817 A1 | 6/2005 | Yazaki et al. |
| 2006/0052700 A1 | 3/2006 | Svanerudh |
| 2006/0074318 A1 | 4/2006 | Ahmed et al. |
| 2006/0122537 A1 | 6/2006 | Reynolds et al. |
| 2007/0010726 A1 | 1/2007 | Loeb |
| 2007/0055162 A1 | 3/2007 | Mahos |
| 2008/0119758 A1 | 5/2008 | Samuelsson et al. |
| 2008/0285909 A1 | 11/2008 | Younge et al. |
| 2009/0082678 A1 | 3/2009 | Smith |
| 2009/0088650 A1 | 4/2009 | Corl |
| 2009/0116020 A1 | 5/2009 | Wu et al. |
| 2009/0192412 A1 | 7/2009 | Sela et al. |
| 2009/0226128 A1 | 9/2009 | Donlagic et al. |
| 2010/0022950 A1 | 1/2010 | Anderson et al. |
| 2010/0087605 A1 | 4/2010 | Yamamoto et al. |
| 2010/0145308 A1 | 6/2010 | Layman et al. |
| 2010/0234698 A1 | 9/2010 | Manstrom et al. |
| 2010/0241008 A1 | 9/2010 | Belleville et al. |
| 2011/0046477 A1 | 2/2011 | Hulvershorn et al. |
| 2011/0071407 A1 | 3/2011 | Hübinette et al. |
| 2011/0098572 A1 | 4/2011 | Chen et al. |
| 2011/0152721 A1 | 6/2011 | Sela |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0245808 A1 | 10/2011 | Voeller et al. |
| 2011/0319773 A1 | 12/2011 | Kanz et al. |
| 2012/0083794 A1 | 4/2012 | Martin et al. |
| 2012/0122051 A1 | 5/2012 | Hackel et al. |
| 2012/0210797 A1 | 8/2012 | Yu et al. |
| 2012/0227505 A1 | 9/2012 | Belleville et al. |
| 2012/0238869 A1 | 9/2012 | Schmitt et al. |
| 2012/0245457 A1 | 9/2012 | Crowley |
| 2012/0259273 A1 | 10/2012 | Moshinsky et al. |
| 2012/0265102 A1 | 10/2012 | Leo et al. |
| 2013/0046190 A1 | 2/2013 | Davies |
| 2013/0051731 A1 | 2/2013 | Belleville et al. |
| 2013/0190633 A1 | 7/2013 | Dorando |
| 2013/0218032 A1 | 8/2013 | Belleville |
| 2013/0296718 A1 | 11/2013 | Ranganathan et al. |
| 2013/0296722 A1 | 11/2013 | Warnking et al. |
| 2013/0317372 A1 | 11/2013 | Eberle et al. |
| 2013/0345574 A1 | 12/2013 | Davies et al. |
| 2014/0005558 A1 | 1/2014 | Gregorich |
| 2014/0058275 A1 | 2/2014 | Gregorich et al. |
| 2014/0066789 A1 | 3/2014 | Nishigishi et al. |
| 2014/0081244 A1 | 3/2014 | Voeller et al. |
| 2014/0094691 A1 | 4/2014 | Steinberg et al. |
| 2014/0094693 A1 | 4/2014 | Cohen et al. |
| 2014/0103273 A1 | 4/2014 | Nakajima |
| 2014/0107624 A1 | 4/2014 | Belleville |
| 2014/0121475 A1 | 5/2014 | Alpert et al. |
| 2014/0135633 A1 | 5/2014 | Anderson et al. |
| 2014/0180028 A1 | 6/2014 | Burkett |
| 2014/0205235 A1 | 7/2014 | Benjamin et al. |
| 2014/0207008 A1 | 7/2014 | Davies |
| 2014/0241669 A1 | 8/2014 | Belleville et al. |
| 2014/0248021 A1 | 9/2014 | Belleville et al. |
| 2014/0276109 A1 | 9/2014 | Gregorich |
| 2014/0276142 A1 | 9/2014 | Dorando |
| 2014/0309533 A1 | 10/2014 | Yamashika |
| 2014/0350414 A1 | 11/2014 | McGowan et al. |
| 2015/0003783 A1 | 1/2015 | Benjamin et al. |
| 2015/0003789 A1 | 1/2015 | Webler |
| 2015/0025330 A1 | 1/2015 | Davies et al. |
| 2015/0025398 A1 | 1/2015 | Davies et al. |
| 2015/0032011 A1 | 1/2015 | McGowan et al. |
| 2015/0051499 A1 | 2/2015 | McGowan |
| 2015/0078714 A1 | 3/2015 | Isenhour |
| 2015/0080749 A1 | 3/2015 | Anderson et al. |
| 2015/0112210 A1 | 4/2015 | Webler |
| 2015/0119705 A1 | 4/2015 | Tochterman et al. |
| 2015/0133800 A1 | 5/2015 | McCaffrey |
| 2015/0141842 A1 | 5/2015 | Spanier |
| 2015/0161790 A1 | 6/2015 | Takahashi et al. |
| 2015/0164467 A1 | 6/2015 | Suetoshi et al. |
| 2015/0198774 A1 | 7/2015 | Lin et al. |
| 2015/0230713 A1 | 8/2015 | Merritt et al. |
| 2015/0230714 A1 | 8/2015 | Davies et al. |
| 2015/0301288 A1 | 10/2015 | Thornton, Jr. |
| 2015/0305633 A1 | 10/2015 | McCaffrey |
| 2015/0323747 A1 | 11/2015 | Leigh et al. |
| 2016/0008084 A1 | 1/2016 | Merritt et al. |
| 2016/0135757 A1 | 5/2016 | Anderson et al. |
| 2016/0135787 A1 | 5/2016 | Anderson et al. |
| 2016/0136392 A1 | 5/2016 | Wenderow et al. |
| 2016/0157787 A1* | 6/2016 | Merritt ............... A61B 5/02007 600/481 |
| 2016/0157802 A1 | 6/2016 | Anderson |
| 2016/0157803 A1 | 6/2016 | Keller |
| 2016/0157807 A1 | 6/2016 | Anderson et al. |
| 2016/0166327 A1 | 6/2016 | Keller |
| 2016/0206214 A1 | 7/2016 | Davies et al. |
| 2016/0262627 A1 | 9/2016 | Hecker et al. |
| 2017/0065225 A1 | 3/2017 | Hanson et al. |
| 2018/0192983 A1 | 7/2018 | Dascal et al. |
| 2018/0263507 A1 | 9/2018 | Merritt et al. |
| 2018/0354106 A1* | 12/2018 | Moore ..................... G01L 5/24 |
| 2019/0083046 A1 | 3/2019 | Alpert et al. |

FOREIGN PATENT DOCUMENTS

| | | |
|---|---|---|
| EP | 0235992 A1 | 9/1987 |
| EP | 0738495 A1 | 10/1996 |
| EP | 0879615 A1 | 11/1998 |
| EP | 0879617 A1 | 11/1998 |
| EP | 1039321 A2 | 9/2000 |
| EP | 0750879 B1 | 11/2000 |
| EP | 1136032 A1 | 9/2001 |
| EP | 1136036 A1 | 9/2001 |
| EP | 1136036 B1 | 2/2003 |
| EP | 1136032 B1 | 9/2003 |
| EP | 1479407 A1 | 11/2004 |
| EP | 1925958 A1 | 5/2008 |
| EP | 1927316 A1 | 6/2008 |
| GB | 1440761 A | 6/1976 |
| GB | 2300978 A | 11/1996 |
| JP | S53141644 A | 12/1978 |
| JP | H08257128 A | 10/1996 |
| JP | H08280634 A | 10/1996 |
| JP | H10501339 A | 2/1998 |
| JP | H10337280 A | 12/1998 |
| JP | H1172399 A | 3/1999 |
| JP | H11258476 A | 9/1999 |

(56) References Cited

FOREIGN PATENT DOCUMENTS

| | | |
|---|---|---|
| JP | 2005291945 A | 10/2005 |
| JP | 2008304731 A | 12/2008 |
| JP | 200910182 A | 1/2009 |
| JP | 2010233883 A | 10/2010 |
| JP | 2012233883 A | 10/2010 |
| JP | 2013132886 A | 7/2013 |
| JP | 201442645 A | 3/2014 |
| WO | 9313707 A1 | 7/1993 |
| WO | 9533983 A1 | 12/1995 |
| WO | 9626671 A1 | 9/1996 |
| WO | 9945352 A1 | 9/1999 |
| WO | 2007058616 A1 | 5/2007 |
| WO | 2007130163 A1 | 11/2007 |
| WO | 2008034010 A2 | 3/2008 |
| WO | 2008076931 A2 | 6/2008 |
| WO | 2009042865 A1 | 4/2009 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2012091783 A1 | 7/2012 |
| WO | 2013033489 A1 | 3/2013 |
| WO | 2014025255 A1 | 2/2014 |
| WO | 2015059311 A1 | 4/2015 |
| WO | 2016005944 A1 | 1/2016 |
| WO | 2017013020 A1 | 1/2017 |

OTHER PUBLICATIONS

Application filed Apr. 3, 2014 for U.S. Appl. No. 14/196,740.
International Search Report and Written Opinion dated Oct. 22, 2018 for International Application No. PCT/US2018/044153.
Van'T Veer et al., "Comparison of Different Diastolic Resting Indexes to iFR. Are They Equal?", Journal of American College of Cardiology, 70(25): 3088-3096, Dec. 18, 2017.
Jaroslaw et al., "Two Stage EMG Onset Detection Method", Archives of Control Sciences, 22(4): 427-440, Dec. 1, 2012.
International Search Report and Written Opinion dated May 7, 2019 for International Application No. PCT/US2019/019247.
Matsuo et al; "Visualization of the Improvement of Myocradial Perfusion after Coronary Intervention using Motorized fractional Flow Reserve Pullback Curve." Cardiovascular Intervention and Therapeutics, vol. 33, No. 2, 2018.
International Search Report and Written Opinion dated Jun. 19, 2019 for International Application No. PCT/US2019/027512.
International Search Report and Written Opinion dated Jul. 3, 2019 for International Application No. PCT/US2019/023488.
International Search Report and Written Opinion dated Jul. 8, 2019 for International Application No. PCT/US2019/026055.

* cited by examiner

METHODS FOR ASSESSING A VESSEL WITH SEQUENTIAL PHYSIOLOGICAL MEASUREMENTS

CROSS-REFERENCE TO RELATED APPLICATIONS

This application is a continuation of U.S. application Ser. No. 16/283,235, filed Feb. 22, 2019, which claims the benefit of priority under 35 U.S.C. §119 of U.S. Provisional Application No. 62/634,501, filed Feb. 23, 2018, the entire disclosure of which is hereby incorporated by reference.

TECHNICAL FIELD

The present disclosure pertains to medical devices, medical systems, and methods for using medical systems and devices. More particularly, the present disclosure pertains to devices, systems, and methods configured for use in assessing the severity of one or more blockages in a blood vessel.

BACKGROUND

A wide variety of intracorporeal medical devices, systems, and methods have been developed for medical use, for example, intravascular use. Some of these devices and systems include guidewires, catheters, processors, displays, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices and systems as well as alternative methods for manufacturing and using medical devices and systems.

BRIEF SUMMARY

This disclosure provides design, material, manufacturing methods, and use alternatives for medical devices, systems, and methods. An example is a system for evaluating a vessel of a patient using pressure measurements. The system comprises: a processor configured to obtain a first series of pressure measurements from a first instrument within the vessel over a time period while the first instrument is moved longitudinally through the vessel from a first position to a second position, and obtain a second series of pressure measurements from a second instrument positioned within the vessel over the time period while the second instrument remains in a fixed longitudinal position within the vessel. The processor is configured to calculate a series of pressure ratio values using the first pressure measurements and the second pressure measurements, and generate a pressure ratio curve for the time period using the series of pressure ratio values. The processor is configured to identify a stepped change in the pressure ratio curve using an automatic step detection (ASD) process. The ASD includes: identifying a general position of a starting point of the stepped change by identifying a change in the pressure ratio values within a first window along the pressure ratio curve that is at or above a first threshold change value; and identifying an optimized position of the starting point by identifying a change in the pressure ratio values within a second window along the pressure ratio curve that is at or above a second threshold change value, wherein the second window is smaller than the first window, and the second threshold change value is smaller than the first threshold change value.

Alternatively or additionally to any of the embodiments above or below, the automatic step detection process further includes identifying a general position of an ending point of the stepped change by identifying a change in the pressure ratio values within a third window along the pressure ratio curve that is at or below a third threshold change value.

Alternatively or additionally to any of the embodiments above or below, the automatic step detection process further includes identifying an optimized position of the ending point along the curve by identifying a change in the pressure ratio values within a fourth window along the pressure ratio curve that is at or below a fourth threshold change value, wherein the fourth window is smaller than the third window, and the fourth threshold change value is smaller than the third threshold change value.

Alternatively or additionally to any of the embodiments above or below, the system further includes a display, and wherein the processor is configured to output to the display a visual representation of the pressure ratio curve.

Alternatively or additionally to any of the embodiments above or below, wherein the processor is configured to output to the display a starting point indicator at the optimized position of the starting point of the stepped change on the visual representation of the pressure ratio curve.

Alternatively or additionally to any of the embodiments above or below, wherein the processor is configured to output to the display an ending point indicator at the optimized position of the ending point of the stepped change on the visual representation of the pressure ratio curve.

Alternatively or additionally to any of the embodiments above or below, wherein the processor is configured to output to the display a step amplitude label showing the difference between the starting point and the ending point of the stepped change on the visual representation of the pressure ratio curve.

Alternatively or additionally to any of the embodiments above or below, wherein the stepped change is a stepped increase in the pressure ratio curve.

Alternatively or additionally to any of the embodiments above or below, wherein identifying the stepped change in the pressure ratio curve using the automatic step detection process occurs in real time relative to obtaining the first series of pressure measurements and the second series of pressure measurements.

Alternatively or additionally to any of the embodiments above or below, wherein the first and third threshold change values are the same in magnitude, wherein the first and third windows are the same in duration, or both.

Alternatively or additionally to any of the embodiments above or below, wherein the second and fourth threshold change values are the same in magnitude, wherein the second and fourth windows are the same in duration, or both.

Alternatively or additionally to any of the embodiments above or below, wherein the first threshold change value has a magnitude in the range of 0.01 to 0.05, wherein the second threshold change value has a magnitude in the range of 0.004 to 0.009, or both.

Alternatively or additionally to any of the embodiments above or below, wherein the first window is in the range of 3 to 6 heartbeats, the second window is in the range of about 1 to 3 heartbeats, or both.

Alternatively or additionally to any of the embodiments above or below, further including identifying one or more additional stepped changes in the curve using the automatic step detection process.

Alternatively or additionally to any of the embodiments above or below, wherein the pressure ratio values comprise FFR values, iFR values, dFR values, or resting Pd/Pa values.

Another example system fix evaluating a vessel of a patient comprises a display, and a processor in communication with the display. The processor is configured to obtain a first series of pressure measurements from a first instrument within the vessel over a time period while the first instrument is moved longitudinally through the vessel from a first position to a second position, and obtain a second series of pressure measurements from a second instrument positioned within the vessel over the time period while the second instrument remains in a fixed longitudinal position within the vessel. The processor is configured to calculate a series of pressure ratio values using the first pressure measurements and the second pressure measurements, generate a pressure ratio curve using the series of pressure ratio values, and output the pressure ratio curve to the display. The processor is also configured to identify a stepped change in the pressure ratio curve using an automatic step detection (ASD) process. The ASD process includes: identifying a general position of a starting point of the stepped change by identifying a change in the pressure ratio values within a first window along the pressure ratio curve that is above a first threshold change value; identifying an optimized position of the starting point by identifying a change in the pressure ratio values within a second window along the pressure ratio curve that is above a second threshold change value, wherein the second window is smaller than the first window, and the second threshold change value is smaller than the first threshold change value; identifying a general position of an ending point of the stepped change by identifying a change in the pressure ratio values within a third window along the pressure ratio curve that is below a third threshold change value; and identifying an optimized position of the ending point by identifying a change in the pressure ratio values within a fourth window along the pressure ratio curve that is below a fourth threshold change value, wherein the fourth window is smaller than the third window, and the fourth threshold change value is smaller than the third threshold change value. The processor may output to the display marks on the pressure ratio curve indicating the location of the starting point and ending point of the stepped change in the pressure ratio curve.

Alternatively or additionally to any of the embodiments above or below, the system may further include the first instrument, and the first instrument comprises a pressure sensing guidewire.

Alternatively or additionally to any of the embodiments above or below, the system may further include a pullback mechanism, and the pullback mechanism is configured to move the first instrument longitudinally through the vessel from the first position to the second position.

Alternatively or additionally to any of the embodiments above or below, wherein the stepped change is a stepped increase in the pressure ratio curve.

Alternatively or additionally to any of the embodiments above or below, wherein the processor is configured to identify additional stepped increases in the curve using the automatic step detection process.

Some embodiment may include a method of evaluating a vessel of a patient. Thee method comprises: obtaining a first series of pressure measurements from a first instrument within the vessel over a time period while the first instrument is moved longitudinally through the vessel from a first position to a second position; obtaining a second series of pressure measurements from a second instrument positioned within the vessel over the time period while the second instrument remains in a fixed longitudinal position within the vessel; calculating a series of pressure ratio values using the first pressure measurements and the second pressure measurements; generating a pressure ratio curve using the series of pressure ratio values; identifying a stepped change in the pressure ratio curve using an automatic step detection (ASD) process. The ASD process including: identifying a general position of a starting point of the stepped change by identifying a change in the pressure ratio values within a first window along the pressure ratio curve that is above a first threshold change value; and identifying an optimized position of the starting point by identifying a change in the pressure ratio values within a second window along the pressure ratio curve that is above a second threshold change value, wherein the second window is smaller than the first window, and the second threshold change value is smaller than the first threshold change value.

Alternatively or additionally to any of the embodiments above or below, wherein the ASD process further includes identifying a general position of an ending point of the stepped change by identifying a change in the pressure ratio values within a third window along the pressure ratio curve that is below a third threshold change value.

Alternatively or additionally to any of the embodiments above or below, wherein the ASD process further includes optimizing the position of the ending point along the curve by identifying a change in the pressure ratio values within a fourth window along the pressure ratio curve that is below a fourth threshold change value, wherein the fourth window is smaller than the third window, and the fourth threshold change value is smaller than the third threshold change value.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
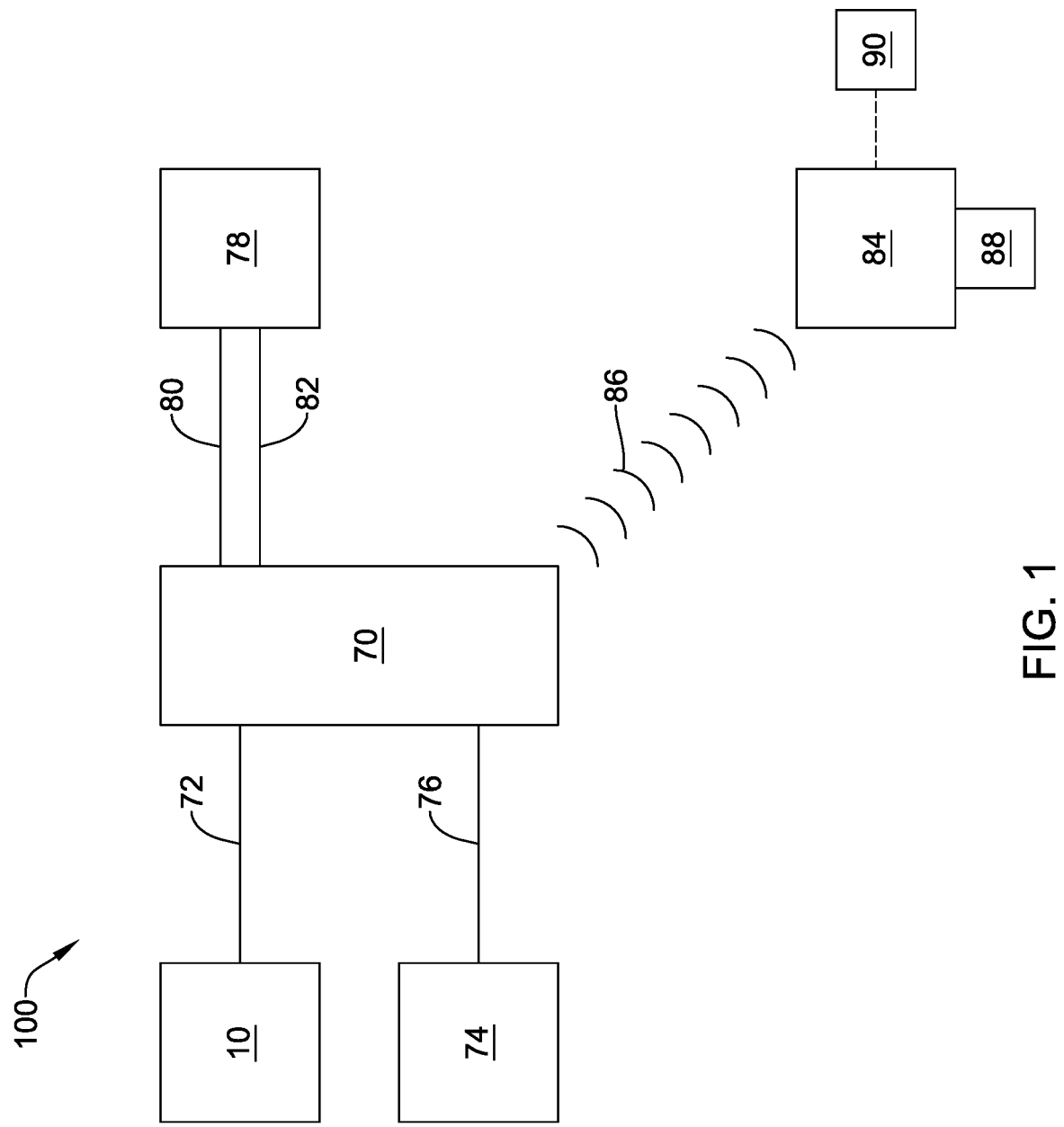
FIG. 1 schematically illustrates an example system that may be used for assessing a blood vessel.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions and/or diagnostic procedures, it may be desirable to provide a physiological assessment of the hemodynamic impact of one or more stenosis within a blood vessel. Such an assessment may be achieved by obtaining pressure measurements from within the vessel from both a first instrument positioned distal of an area of interest, such as one or more stenoses, and a second instrument positioned proximal of the area of interest. The pressure differential between the two pressure measurements within the vessel (e.g. the distal pressure measurement and the proximal pressure measurement) can be used to calculate a pressure ratio of the two pressure measurements (the distal pressure measurement divided by the proximal pressure measurement). Such pressure ratios can be useful in assessing the hemodynamic impact of one or more stenosis within a blood vessel. In the context of this application, these ratios can be collectively and generally referred to as pressure ratio values. As used herein, the distal pressure measurement may often be referred to as $P_d$, and the proximal pressure measurement, which is the aortic pressure, may often be referred to as $P_a$.

Some examples of such useful pressure ratios include Factional Flow Reserve (FFR), resting whole-cycle distal pressure/proximal pressure (resting $P_d/P_a$), resting distal pressure/proximal pressure during diastole (dPR), Instantaneous Wave-free Ratio (iFR), or the like. These ratios may be useful, for example, for assessing the hemodynamic impact of a stenosis in a coronary artery. FFR is the pressure ratio ($P_d/P_a$) calculated by using average mean pressure measurements over a number of heartbeats over the whole cardiac cycle under the influence of a hyperemic agent, such as adenosine. Resting $P_d/P_a$ is the pressure ratio ($P_d/P_a$) calculated using average mean pressure measurements over a number of heartbeats over the whole cardiac cycle at rest (e.g. without the influence of a hyperemic agent). dPR is the pressure ratio ($P_d/P_a$) calculated by using average mean pressure measurements over a number of heartbeats made during diastole. iFR is the pressure ratio ($P_d/P_a$) calculated by using average mean pressure measurements over a number of heartbeats restricted to an identified wave-free period during diastole. As such, each of these different pressure ratios may be understood as the ratio of $P_d/P_a$, with the difference among them being the timing parameters and conditions under which the underlying proximal and distal pressure measurements are made.

By comparing the calculated pressure ratio value to a threshold or predetermined value, medical personnel can be aided in determining if interventional treatment is necessary or warranted. For example, in the context of assessing the hemodynamic impact of a coronary stenosis, a pressure ratio value below a threshold value of 0.8 is indicative of stenosis potentially worthy of more aggressive or invasive treatments, such as angioplasty or stenting, while a pressure ratio value at or above the 0.8 threshold value may indicate stenosis (or lack thereof) potentially worthy of less aggressive or less invasive treatments, such as drug therapy or no treatment at all. While the above examples are representative of pressure ratios values that may be used in the coronary vasculature, the devices, systems, and methods described herein may also be used in a wide variety of other vascular applications. Other vascular applications may include the peripheral vasculature, including lower limb, carotid, and neurovascular; renal vasculature; and/or venous vasculature.

In some instances, it is useful to obtain and/or calculate a series of pressure ratio values in an area of interest along a portion of the length of a vessel. Significant and/or rapid stepped changes in the pressure ratio values along a portion of the length of the vessel can indicate one or more significant or focal stenosis at certain location(s) within the vessel. This may be particularly valuable in a case having a complex stenosis and/or series of stenoses along a portion of the length of the vessel. To obtain the pressure measurement data to calculate the series of pressure ratio values along a portion of a length of the vessel, the underlying distal and proximal pressure measurements, e.g., $P_d$ and $P_a$, may be obtained over a period of time while one of the pressure measuring instrument, typically the instrument making the distal pressure measurements, is moved longitudinally from one side and through the area of interest in the vessel, while the other pressure measuring instrument, typically the instrument making the proximal pressure measurements, remains stationary on the other side of the area of interest in the vessel. The moving instrument is typically moved longitudinally though the area of interest, e.g., the stenosed area, proximally back toward the stationary instrument. Such a procedure may be referred to as a "pullback". However, it is contemplated that in other embodiments, the moving instrument may start close to or adjacent to the stationary instrument, and be moved longitudinally away from the stationary instrument, and distally though the area of interest. Such a procedure may be referred to as a "push-though".

It is often useful to generate a pressure ratio curve using the series of pressure ratio values obtained during the pullback and/or push-through. The pressure ratio curve, showing the pressure ratio values over the time period of the pullback or push-through, can be used to identify significant stepped changes (e.g., more focused or larger or more aggressive or more rapid stepped changes) in the pressure ratio values along a portion of the length of the vessel, as opposed to less significant changes (e.g., less focused or smaller or less aggressive or more gradual changes) in the pressure ratio values. The changes in the pressure ratio curve within a given window can be compared to certain set (e.g., predetermined) threshold values to identify significant stepped changes relative to less significant stepped changes. During a pullback procedure, the stepped changes above a certain/predetermined threshold will be represented by significant increases in the pressure ratio values within a certain window. However, the opposite would be true during a push-through, in which case the stepped changes above a certain/predetermined threshold will be represented by significant decreases in the pressure ratio values within a window. The more significant stepped changes along the pressure ratio curve may be used to identify the presence of significant (e.g., more focused or larger or more aggressive) stenosed areas that can then be the focus for more aggressive treatment options. The less significant changes in the pressure ratio curve may be used to identify the presence of less significant (e.g., less focused or smaller or less aggressive or more gradual) stenosed areas that can then be the focus for less aggressive treatment, or no treatment at all.

One problem and/or difficulty that may be associated with using a pressure ratio curve in this analysis is involved in the accurate and/or consistent identification, and potential labeling of, significant stepped changes in the pressure ratio curve, which may then be used to identify the presence of one or more significant stenosed areas for treatment. In particular, it may be desirable to provide for the accurate and/or consistent identification of, and optionally the labeling of, the beginning and/or ending locations of significant stepped increases in the pressure ratio curve. It may also be desirable to determine, indicate and/or label the size or amplitude of certain significant stepped changes in the pressure ratio curve. It may also be desirable to have a system and/or process to consistently identify what may be considered a "significant" stepped change, and what may be a considered a "less significant" stepped change in the pressure ratio curve. For example, it may be desirable to set and apply consistent threshold value(s) for the determination of the general location of starting and/or ending locations of significant stepped increases in the pressure ratio curve. It may also be desirable to consistently optimize the position of the starting and/or ending points of significant stepped increases in the pressure ratio curve. For example, it may be desirable to set and apply consistent threshold value(s) for the determination of the optimized location of starting and/or ending locations of significant stepped increases in the pressure ratio curve. Such a system and/or process may be used to better identify the start and stop of significant stenosed areas for treatment.

In that context, disclosed herein is an Automatic Step Detection (ASD) process and/or algorithm that may be used to help resolve these problems and/or difficulties, and achieve desired results (e.g. the identification and/or labeling of starts and/or ends and/or amplitudes of significant stepped changes in the pressure ratio curve). The ASD process consistently applies threshold value(s) within set window(s) to identify the general starting and/or ending locations of significant stepped changes in the pressure ratio curve. The ASD process may also consistently apply set threshold value(s) within set window(s) to optimize the position of starting and/or ending locations of significant stepped changes in the pressure ratio curve.

Methods and systems are disclosed herein that use the ASD process and/or algorithm. For example, a method for analyzing a vessel may include obtaining pressure measurements (e.g., $P_d$ and $P_a$) from instruments during the pullback and/or push-though, calculating a series of pressure ratio values, generating a pressure ratio curve, and identifying if there are one or more significant stepped changes in the pressure ratio curve using the ASD process and/or algorithm. Some example systems disclosed herein include a processor that is configured to perform such a method, including the use of the ASD process and/or algorithm. Some example embodiments of systems, methods, and processors, including a more detailed discussion of the ASD process and/or algorithm, are set forth in more detail herein.

Reference is now made to the figures for a discussion of some illustrative embodiments. An example system 100 is schematically represented in FIG. 1. The system 100 may be configured for assessing/determining pressure ratios, for example, FFR, iFR, dPR, or resting Pd/Pa, or the like, either statically or during a pullback procedure. The system 100 may include a first pressure sensing medical device 10. In at least some instances, the first pressure sensing medical device 10 may take the form of a pressure sensing guidewire 10. Some additional detail regarding an example of such a guidewire 10 is disclosed below, and shown in FIG. 5. In other instances, the first pressure sensing medical device 10 may be a catheter or other type of pressure sensing medical device. The pressure sensing medical device 10 may be utilized to measure blood pressure distal of an area of interest, such as one or more intravascular stenosis, (e.g., measure the distal pressure $P_d$). The first pressure sensing medical device 10 can be configured to measure blood pressure while stationary, or while being moved longitudinally through a vessel from a first location to a second location. As such, the first pressure sensing medical device 10 may be moved longitudinally within the vessel during a "pullback" or "push-through" procedure.

In some embodiments, the system 100 may include a device or mechanism (not shown) to impart longitudinal movement to the first pressure sensing medical device 10, for example, during a pullback or push-through procedure. In some embodiments, the pullback/push-through device or mechanism may be configured to engage and impart longitudinal movement to the first pressure sensing medical device 10 at a continuous speed and/or for a set distance. In some embodiments, the pullback/push-through device is configured to move the first pressure sensing medical device 10 at a variable speed and/or in a stepwise or intermittent manner, optionally in coordination with the heartbeat of a patient. In some embodiments, the system 100 does not include a pullback or push-though device, but rather, the first pressure sensing medical device 10 may be moved longitudinal through the vessel manually by the operator, as necessary or desired.

The first pressure sensing medical device 10 may be coupled to a linking device 70. In some instances, this may include directly attaching the first pressure sensing medical device 10 to the linking device 70. In other instances, another structure such as a connector cable (not shown) may be used to couple the first pressure sensing medical device 10 to the linking device 70. When the first pressure sensing medical device 10 is coupled to the linking device 70, a first pressure data 72 may be communicated between the first pressure sensing medical device 10 and the linking device 70. It is noted that in FIG. 1, a line is drawn between the first pressure sensing medical device 10 and the linking device 70 to represent the coupling of the first pressure sensing medical device 10 and the linking device 70. In addition the line between the first pressure sensing medical device 10 and the linking device 70 is labeled with reference number 72 in order to represent the transmission of the first pressure data 72 (and/or the first pressure data 72 itself). In at least some instances, the first pressure data 72 is the distal pressure $P_d$.

The system 100 may also include a second pressure sensing medical device 74. In at least some instances, the second pressure sensing medical device 74 may take the form of a pressure sensing catheter. However, other devices are contemplated including pressure sensing guidewires or other devices. The second pressure sensing medical device 74 may be utilized to measure blood pressure, for example, proximal of an area of interest. In some cases, second pressure sensing medical device 74 may be utilized to measure the aortic pressure. The second pressure sensing medical device 74 may be configured to remain stationary during use, for example, during a pullback or push-through procedure.

The second pressure sensing medical device 74 may also be coupled to the linking device 70 and may communicate a second pressure data 76 between the second pressure sensing medical device 74 and the linking device 70. It is noted that in FIG. 1, a line is drawn between the second pressure sensing medical device 74 and the linking device 70 to represent the coupling of the second pressure sensing medical device 74 and the linking device 70. In addition the line between the second pressure sensing medical device 74 and the linking device 70 is labeled with reference number 76 in order to represent the transmission of the second pressure data 76 (and/or the second pressure data 76 itself). In at least some instances, the second pressure data 76 is the proximal pressure, such as aortic pressure, $P_a$.

In some instances, the linking device 70 may communicate with a hemodynamic system 78 (e.g., a hemodynamic display system 78). When doing so, data representative of the distal pressure $P_d$ (represented by reference number 80) may be communicated to the hemodynamic system 78 and data representative of the aortic pressure $P_a$ (represented by reference number 82) may be communicated to the hemodynamic system 78. In some instances, both connections between the linking device 70 and the hemodynamic system 78 (e.g., for communicating $P_d$ and $P_a$) may be wired connections. In other instances, one or both of the connections may be wireless connections. In still other instances, both $P_d$ and $P_a$ may be communicated along a single wired connection.

In some instances, the linking device 70 may also communicate with a processing and/or display system 84. When doing so, data representative of the distal pressure $P_d$ and data representative of the proximal, or aortic pressure $P_a$ (both the distal pressure $P_d$ and the aortic pressure $P_a$ data are represented by reference number 86 in FIG. 1) may be communicated to the processing and/or display system 84. In at least some instances, $P_d$ and $P_a$ may be communicated between the linking device 70 and the processing and/or display system 84 using a wireless connection. In other instances, one or both of $P_d$ and $P_a$ may be communicated between the linking device 70 and the processing and/or display system 84 with a wired connection.

The processing and/or display system 84 may include a processor 88. The processor 88 may be an integrated component of the processing and/or display system 84 (e.g., the processor 88 may be disposed within the same housing as the processing and/or display system 84) or the processor 88 may be a separate component of the processing and/or display system 84 and coupled therewith. The processor 88 may be coupled to the first pressure sensing medical device 10 and coupled to the second pressure sensing medical device 74 and may be configured such that first and second pressure measurements (e.g., $P_d$ and $P_a$) may be received and/or obtained by the processor 88 from the pressure sensing medical devices 10 and 74. The processor 88 may be configured to receive and/or obtain the first and second pressure measurements while the pressure sensing medical devices remain stationary in the vessel, or wherein at least one of the pressure sensing medical devices is moved longitudinally within the vessel. (e.g. during a pullback or push-though). For example, the processor 88 may be configured to receive and/or obtain a first series of pressure measurements from the first pressure sensing medical device 10 over a time period while it is moved longitudinally through the vessel, and configured to receive and/or obtain a second series of pressure measurements from the second pressure sensing medical device 74 over the time period, while the second device remains in a fixed longitudinal position within the vessel.

The processor 88 may be configured to and/or otherwise be capable of performing a number of calculations, executing instructions, etc. For example, the processor 88 may be configured to calculate/determine the mean distal pressure $P_d$ (e.g., as measured by the first pressure sensing medical device 10 over one or more cardiac cycles), calculate/determine the mean proximal pressure $P_a$ (e.g., as measured by the second pressure sensing medical device 74 over one or more cardiac cycles), plot and/or generate a curve showing the distal pressure $P_d$ and/or the proximal pressure $P_a$ over time, calculate/determine the slope of the plot of the distal pressure $P_d$ and/or the slope of the plot of the proximal pressure $P_a$ (e.g., at various points along the plot), or the like. The processor 88 may be configured to output any of this information to a display 90, as desired.

The processor 88 may be configured to calculate and/or determine pressure ratio values (e.g. FFR, iFR, dPR, resting Pd/Pa, or the like) given distal pressure $P_d$ and proximal pressure $P_a$ pressure measurements. For example, processor 88 may be configured to calculate one or more, or a series of, pressure ratio values (e.g. $P_d/P_a$), using the pressure measurements received or obtained from the first and second instruments and/or calculated by the processor 88 (e.g., using $P_d$ and $P_a$ measurements obtained from the first and second pressure sensing medical devices 10/74). In some examples, the $P_d$ and $P_a$ measurements are obtained while at least one of the pressure sensing medical devices is moved longitudinally within the vessel (e.g. during a pullback or push-though) and the series of the pressure ratio values represent pressure ratio values along a portion of the length of the vessel. The processor 88 may be configured to plot and/or generate a pressure ratio curve using the series of pressure ratio values. The processor 88 may also be configured to calculate/determine the slope of the pressure ratio curve (e.g., at various points along the pressure ratio curve or plot), or the like. The processor 88 may be configured to output the pressure ratio values and/or the plot and/or generated pressure ratio curve to a display 90.

As suggested herein, a display 90 may be coupled to or otherwise integrated with the processing and/or display system 84. The display 90 may display various data received from first pressure sensing medical device 10 and the second pressure sensing medical device 74, plots, graphs, and/or curves of the pressure data and/or pressure ratios as generated by the processor 88, and may show any marking, labeling, numbering, etc., as desired.

The processing and/or display system 84, including the processor 88, may be configured to use and/or provide raw data and/or calculations, or optionally, may be configured to use and/or provide enhanced data or calculations. For example, the mean distal pressure $P_d$, mean proximal pressure $P_a$, the plot and/or curve showing the distal pressure $P_d$ and/or the proximal pressure $P_a$ over time, the pressure ratio values ($P_d/P_a$), the plot or curve of pressure ratio values over time, or the like, can be used or shown as raw data and/or calculations, or may optionally be filtered, smoothed, enhanced, conditioned and/or otherwise treated by the processor, for example, to remove noise and/or abnormalities. Some examples of filters may include a Moving Maximum Filter, a Median Builder filter, or other generally known filters, or the like.

In some embodiments, the calculations, executing instructions, etc. carried out by the processor 88, including the ASD discussed below, may be made in real time or live, for example, to identify the pressure ratio values and curves, the pressure ratio curve and/or stepped changes in the pressure ratio curve (including the starting point and ending points of the stepped changes) during a procedure. In the context of this application, "real time" or "live" is intended to mean calculations and/or displaying data within 10 seconds of data acquisition. This can include calculations that occur in some cases within 5 seconds, or within 1 second, or even concurrently with data acquisition during a procedure. In some other cases, some or all of the calculations, executing instructions, etc., may occur after some delay after data acquisition. For example, the system may be configured to acquire data, and then at some point in time later, perform calculations and/or display results. For example, the processor 88 may be configured to provide a review and/or playback mode, which occurs some time after data was collected during a procedure, and at least some of the calculations, executing instructions, etc., may display during the review or playback mode.

It is also contemplated that the hemodynamic system 78, the linking device 70, or both, may include a processor, and/or a display and/or a processing and/or display system, similar to the processor 80, display 90, or processing and display system 84 configured as described herein. For example, such processors and/or displays may be configured to carry out the methods and procedures disclosed herein, including the functions and methods described herein, including the ASD process and/or algorithm, as described in more detail below.

The processor 88 may be configured to identify stepped changes in one or more of the curves or plots. For example, the processor 88 may be configured to identify stepped changes (e.g. significant stepped changes at and/or above certain set threshold value(s)) in the pressure ratio curve using an Automatic Step Detection (ASD) process and/or algorithm. The ASD process can be used in the identification and labeling of significant stepped changes in the pressure ratio curve, which may then be used to identify the presence of one or more significant stenosis in the vessel for potential treatment. In particular, the ASD may be used for the identification of, and optionally the labeling of, the beginning and/or ending locations of significant stepped increases in the pressure ratio curve, and may also be used to determine, indicate and/or label the size or amplitude of certain significant stepped changes in the pressure ratio curve.

Figure 2:
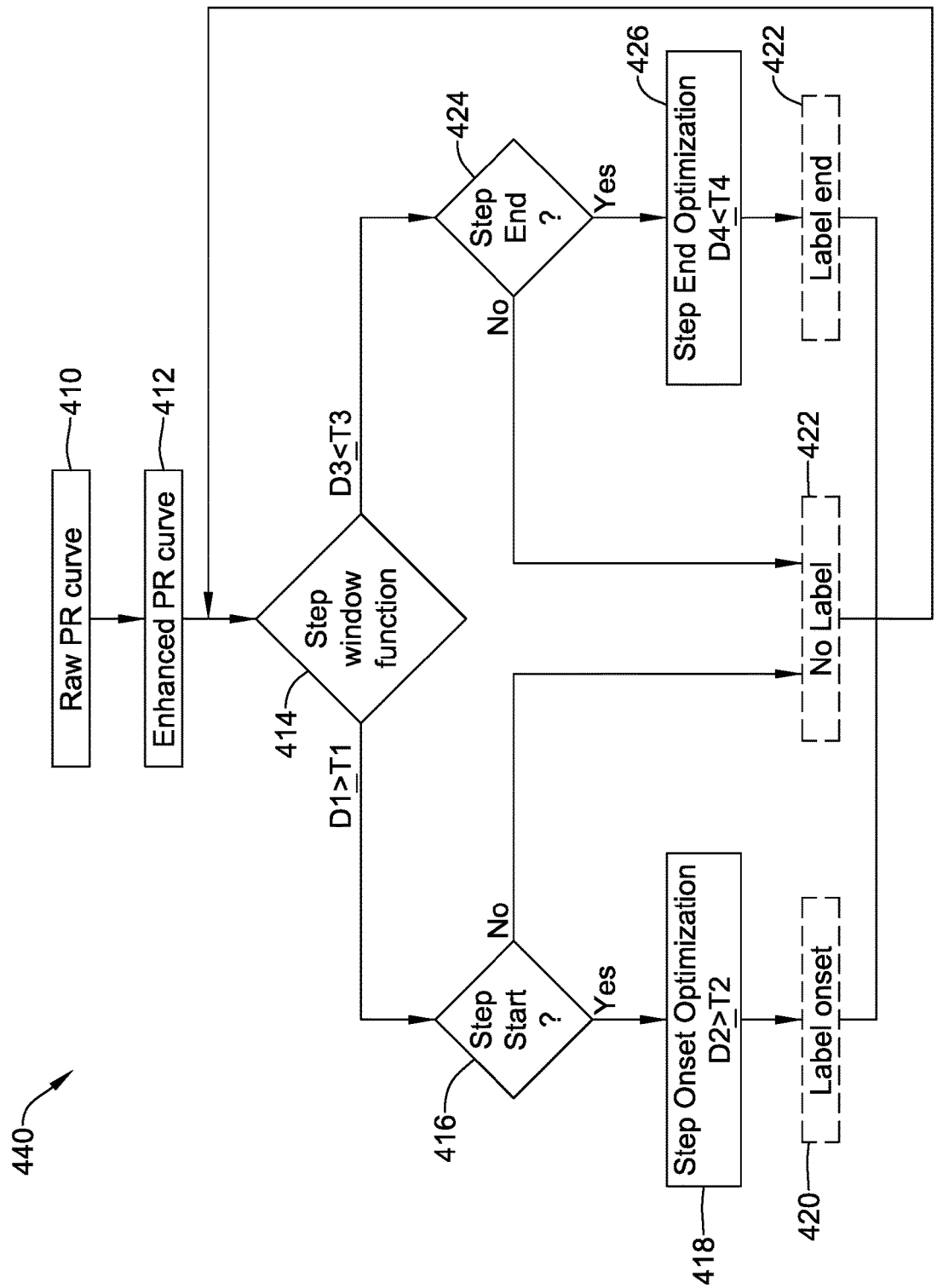
FIG. 2 is an example flow chart diagram showing example steps of an Automatic Step Detection (ASD) process or algorithm.

FIG. 2 shows a flow chart diagram 440 including an example ASD process or algorithm. In this example flow chart, the raw pressure ratio curve 410 is schematically represented in box 410. The raw pressure curve 410 may be calculated/generated by the processor 88, for example, using a series of pressure ratio values that were in turn calculated using pressure measurements (e.g., $P_d$ and $P_a$ measurements) obtained from first and second pressure sensing medical devices 10/74 during a pullback and/or push-through. As shown in box 412, the raw pressure ratio curve 410 may optionally be filtered, smoothed, enhanced, conditioned and/or otherwise treated to remove noise and/or abnormalities in the raw pressure ratio curve 410. In other embodiments, the pressure ratio curve may not be filtered or conditioned, and the raw pressure ratio curve 410 may be used—in which case box 412 may be skipped. The pressure ratio curve (either the raw or enhanced) may be output to the display 84.

The ASD process or algorithm may be used to identify and/or locate one or more stepped change(s) (e.g. significant stepped change above a certain/predetermined threshold value) that may exist in the pressure ratio curve. The ASD includes a Step Window Function (SWF) 414. The SWF 414 incudes identifying a general position of a starting point of a stepped change (e.g. "step start") along the pressure ratio curve by identifying a change in the pressure ratio values within a first window along the pressure ratio curve (e.g. D1) that is at and/or above a first threshold change value (e.g., T1). This is shown in FIG. 2 as the arrow exiting the left side of the SWF box 414, labeled D1>=T1. D1 represents the actual change in the pressure ratio value within the first window along the pressure ratio curve, and T1 represents the first threshold change value that is set when the system is programed. If D1 (the actual change within the first window) is at and/or above T1 (the first threshold), the condition is met for a potential start of a significant stepped change in the pressure ratio curve.

The first window can have a set duration along the pressure ratio curve, and is typically set during programing. Thus, the first window has a duration and/or width along the pressure ratio curve, and D1 is the value that represents the actual change in the pressure ratio value over the given duration of the first window along the pressure ratio curve. The duration of the first window can be chosen as desired, and may be measured in units as desired, for example, time (e.g. seconds, minutes, etc.) or possibly in physiological terms (e.g. heartbeats, breaths, etc.). In some embodiments, the first window will have a duration in the range of 2-10 heartbeats, 2-8 heartbeats, 3-5 heartbeats, or in some cases, 4 heartbeats. In some cases, the first window duration can be measured and/or set in seconds, for example, in the range of 2-30 seconds, 2-20 seconds, 3-10 seconds, 3-5 seconds, or as desired.

The first threshold T1 and the actual change value in the first window D1 will generally be unit-less, as they simply represent change in the pressure ratio value within the first window. The threshold value T1, can be chosen as desired, given the duration of the first window. Generally, the threshold value T1 value is set at a level that will indicate a significant change in the pressure ratio value within the given first window, which in turn would indicate a significant stenosis within the vessel. As such, the threshold value T1 is generally set during programming at a level that will indicate a clinically significant change in the pressure ratio value within the duration of the first window. In some embodiments, threshold value T1 may be set in the range of 0.01 to 0.06, or in the range of 0.02 to 0.05, or in the range of 0.025 to 0.04.

If the D1>=T1 condition is met in the Step Window Function (SWF) 414, the ASD process may then be used to make a determination if the identified D1>=T1 condition indicates the start of a step (e.g. general position of a starting point of a stepped change). This is represented by the "Step Start?" box 416 of the flow chart. If a step start condition already currently exists, and there has not yet been a step end detected (as discussed below), then the current detected D1>=T1 condition is not treated like a step start (as a step start already exists—without an end). As such, the "Step Start?" question is answered as "No", and no step start is identified, no label is attached, as indicated by box 422 of the flow chart, and the process feeds back to the Step Window Function, and starts again, as indicated by the arrow looping from the box 422 back up to the Step Window Function 414.

If, however, a start step does not previously exist, or if a step start previously exists but had a corresponding step end identified and associated therewith (e.g. a previously identified stepped increase with a starting point and an ending point), then the current detected D1>=T1 condition is treated as a step start. As such, the "Step Start?" question in box 416 is answered as "Yes", and proceeds to the "Step Onset Optimization" as represented by box 418.

The "Step Onset Optimization" (SOO) function, represented by box 418 on the flowchart, includes identifying an optimized position of the starting point of the stepped change (e.g. the point on the pressure ratio curve where the significant step first started) by identifying a change in the pressure ratio values within a second window along the pressure ratio curve (e.g. D2) that is at or above a second threshold change value, T2, wherein the second window is smaller than the first window, and the second threshold change value T2 is smaller than the first threshold change value T1. In essence, the SOO function further refines and/or optimizes the position of the starting point of the stepped change in the pressure ratio curve by focusing in on a tighter window than the first window, and looking for a change value that meets a smaller threshold (e.g. T2) than the first threshold (e.g. T1).

The second window can have a set duration along the pressure ratio curve, and is set during programing. The second window has a duration and/or width along the pressure ratio curve, and generally overlaps with and/or includes the portion of the pressure ratio curve that contains the general position of a starting point of a stepped change (e.g. Step Start) as identified by the SWF. In essence, the second window "zooms in" on the pressure ratio curve along a region where the general position of a starting point was identified in the first window during the SWF. The duration of the second window can be chosen as desired, and may be measured in units as desired, for example, those units given for the first window. The second window will be smaller than the first window. In some embodiments, the second window will have a duration in the range of 1-5 heartbeats, 1-3 heartbeats, or in some cases, 2 heartbeats. In other cases, the second window duration can be measured and/or set in seconds, for example, in the range of 1-10 seconds, 1-5 seconds, 1-3 seconds, or in some cases, 2 seconds.

Threshold T2 and the actual change value D2 will generally be unit-less, as they simply represent change in the pressure ratio value within the second window. The second threshold value T2, can be chosen as desired, given the duration of the second window. Generally, the T2 value is set at a level that will indicate a significant change in the pressure ratio value within the given second window, which in turn would indicate a start of a significant stenosis within the vessel. As such, the threshold value T2 is generally set during programming at a level that will indicate a clinically significant change in the pressure ratio value within the duration of the given second window. In some embodiments, threshold value T2 may be set in the range of 0.002 to 0.012, or in the range of 0.004 to 0.01, or in the range of 0.006 to 0.008.

The Step Onset Optimization (SOO) 418 identifies a more specific and/or optimized location along the pressure ratio curve where the condition D2>=T2 is first met, and then identifies this point as the more specific and/or optimized location of the start of the stepped increase. Once the optimized location is identified, the process may include labeling this point accordingly, as the step onset, as shown in box 420. The optimized step start location and/or label may be output to the display, for example, to show the step start in conjunction with the pressure ratio curve. The process then feeds back to the Step Window Function 414, and starts again, as indicated by the arrow looping back up to the Step Window Function. In particular, the process may then be used to identify and optimize the location of a step end to associate with the then identified step start, to thereby define the parameters of the stepped increase.

In that regard, the ASD process may further include identifying a general position of an ending point of the stepped change by identifying a change in the pressure ratio values within a third window along the pressure ratio curve that is below a third threshold change value. For example, the SWF 414 incudes the function to identify a general position of an ending point of a stepped change (e.g. step end) along the pressure ratio curve by identifying a change in the pressure ratio values within a third window along the pressure ratio curve, D3, that is at or below a third threshold change value T3. This is shown in FIG. 2 as the arrow exiting the right side of the SWF box, labeled D3<=T3. D3 represents the actual change in the pressure ratio value within the third window along the pressure ratio curve, and T3 represents the third threshold change value that is set when the system is programed. If D3 (the actual change within the third window) is at and/or below T3 (the third threshold), the condition is met for a potential end of a stepped change.

The third window can have a set duration along the pressure ratio curve, and is set during programing. Thus, the third window has a duration and/or width along the pressure ratio curve, and D3 is the value that represents the actual change in the pressure ratio value over the given duration of the third window. The duration of the third window can be chosen as desired, and may be measured in units as desired, for example, time (e.g. seconds, minutes, etc.) or possibly in physiological terms (e.g. heartbeats, breaths, etc.). In some embodiments, the third window will have a duration in the range of 2-10 heartbeats, 2-8 heartbeats, 3-5 heartbeats, or in some cases, 4 heartbeats. In other cases, the third window duration can be measured and/or set in seconds, for example, in the range of 2-30 seconds, 2-20 seconds, 3-10 seconds, or as desired.

The third threshold value T3 and the actual change value D3 will generally be unit-less, as they simply represent change in the pressure ratio value within the third window. The threshold value T3, can be chosen as desired, given the duration of the third window. Generally, the T3 threshold value is set at a level such that an actual change value at or below which will indicate a smaller or less significant change in the pressure ratio value within the given third window, which in turn may indicate a less significant stenosed area within the vessel. As such, the threshold value T3 is generally set during programming at a level that will indicate a clinically non-significant change in the pressure ratio value within the duration of the third window. In some embodiments, T3 may be set in the range of 0.01 to 0.06, or in the range of 0.02 to 0.05, or in the range of 0.025 to 0.04.

In some embodiments, the first and third window may have the same duration, and the first and third threshold values, T1 and T3, may also be the same. In such instances, the same threshold value (e.g. T1=T3) is used to determine the general positions of the start and end of the significant step in the pressure ratio curve. A change value (e.g. D1) at and/or above the threshold value would indicate the potential general position of a start of a step, while a change value (e.g. D3) at and/or below the threshold value would indicate the potential general position of an end of a step. As may be appreciated, in these circumstances, the logic in the SWF may be set accordingly, so that only one of the D1 and/or D3 could be equal to the threshold value for the requisite condition to be met. It may be logically desirable that both D1 and D3 change values cannot both be equal to the threshold value (e.g. T1=T3). As such, it may be desirable to modify the equations from those shown in FIG. 2. For example, for the general step start function, the equation may be such that the change value D1 may be greater than or equal to the threshold value (e.g. D1>=T1, as shown), while for the step end function, the change value D3 may simply be less than the threshold value (e.g. D3<T3). Another alternative could be that for the general step start function, the change value D1 may be simply greater than the threshold value (e.g. D1>T1), while for the step end function, the change value D3 may be less than or equal to the threshold value (e.g. D3<=T3, as shown).

Referring to FIG. 2, if the D3<=T3 condition is met in the Step Window Function (SWF) 414, the next potential step in the ASD process may be to make a determination if the D3<=T3 condition indicates the end of a step, as indicated by the "Step End?" box 424 of the flow chart. If a start step condition does not currently exist, then the current detected D3<=T1 condition is not treated as a step end. (e.g. the detected condition cannot be an end, because there was no start). As such, the "Step End?" question in box 424 is answered as "No", and no step end is identified, no label is attached, as indicated by box 422 of the flow chart, and the process feeds back to the Step Window Function, and starts again, as indicated by the arrow looping from the box 422 back up to the Step Window Function 414.

If, however, a step start condition does already currently exist, and there has not yet been a corresponding step end detected for that step start, then the current detected D1<=T1 condition is treated like a Step End (as a step start exists—in need of an end). As such, the "Step End?" question is answered as "Yes", and the process proceeds to the "Step End Optimization" as represented by box 426.

The "Step End Optimization" (SEO) function, represented by box 426, includes identifying an optimized position of the ending point of the stepped increase (e.g. step end) by identifying a change in the pressure ratio values within a fourth window along the pressure ratio curve (e.g. D4) that is at or below a fourth threshold change value (e.g. T4), wherein the fourth window is smaller than the third window, and the fourth threshold change value T4 is smaller than the third threshold change value T3. In essence, the SEO further refines and/or optimizes the position of the ending point of the stepped change in the pressure ratio curve by focusing in on a tighter window than the third window, and looking for a change value that meets a smaller threshold than the third threshold.

The fourth window can have a set duration along the pressure ratio curve, and is set during programing. The fourth window has a duration and/or width along the pressure ratio curve, and generally overlaps with and/or includes the portion of the pressure ratio curve that contains the general position of a ending point of a stepped change (e.g. Step End) identified by the SWF. In essence, the fourth window "zooms in" on the pressure ratio curve along a region where the general position of the ending point was identified in the third window. The duration of the fourth window can be chosen as desired, and may be measured in units as desired, for example, those units given for the third window. The fourth window will be smaller than the third window. In some embodiments, the fourth window will have a duration in the range of 1-5 heartbeats, 1-3 heartbeats, or in some cases, 2 heartbeats. In other cases, the fourth window duration can be measured and/or set in seconds, for example, in the range of 1-10 seconds, 1-5 seconds, 1-3 seconds, or in some cases, 2 seconds.

The T4 threshold and the D4 actual change value will generally be unit-less, as they simply represent change in the pressure ratio value within the fourth window. The fourth threshold value T4, can be chosen as desired, given the duration of the fourth window. Generally, the T4 threshold value is set at a level such that a change value at or below will indicate a smaller or less significant change in the pressure ratio value within the given fourth window, which in turn may indicate a less significant stenosed area within the vessel. As such, the threshold value T4 is generally set during programming at a level that will indicate a clinically less or non-significant change in the pressure ratio value within the duration of the fourth window. In some embodiments, T4 may be set in the range of 0.002 to 0.012, or in the range of 0.004 to 0.01, or in the range of 0.006 to 0.008. As may be appreciated, in some embodiments, the second and fourth window may have the same duration, and the second and fourth threshold values, T2 and T4, may also be the same.

The Step End Optimization (SEO) 426 identifies a more specific and/or optimized location along the pressure ratio curve where the condition D4<=T2 is first met, and then identifies this point as the more specific and/or optimized location of the end of a stepped increase. The process may include labeling this point accordingly, as the step end, as shown in box 422. The optimized step end location and/or label may be output to the display, for example, to show the step end in conjunction with the pressure ratio curve. The location and/or label of the step end may be output to the display, and shown in the appropriate position along the pressure ratio curve. The process then feeds back to the Step Window Function, and starts again, as indicated by the arrow looping from box 422 back up to the Step Window Function 414. In particular, the process may then be used to identify and optimize the location of any additional stepped increases, including identifying and optimizing the location of step starts and step ends of any such additional stepped increases.

As indicated above, the location of stepped increases, including the location of the step starting point and step ending point, may be output to the display, and shown in the appropriate positions along the pressure ratio curve, for example, with a marking or label, or the like. Such marking(s) and/or label(s) may take any desired shape or form of indicators as desired. For example, the marking(s) and/or label(s) may include showing a point, dot, line, star, or other indicator at the location of the step start and/or step end on the pressure ratio curve. The marking(s) and/or label(s) may also include and/or show a numerical indicator, for example showing the pressure ratio value at the particular point where a step start and/or step end is identified on the pressure ratio curve. Additionally, for any particular stepped change that is identified, the processor may calculate parameters associated with that particular stepped change, and output those parameters to the display to be shown in conjunction with the pressure ratio curve. For example, the processor may be configured to calculate the magnitude and/or amplitude of the stepped change (e.g. the difference in the pressure ratio value between the step starting point and the step ending point on the pressure ratio curve), and output this information to the display, for example as a numerical label, shown in conjunction with the particular stepped increase on the pressure ratio curve.

Figure 3:
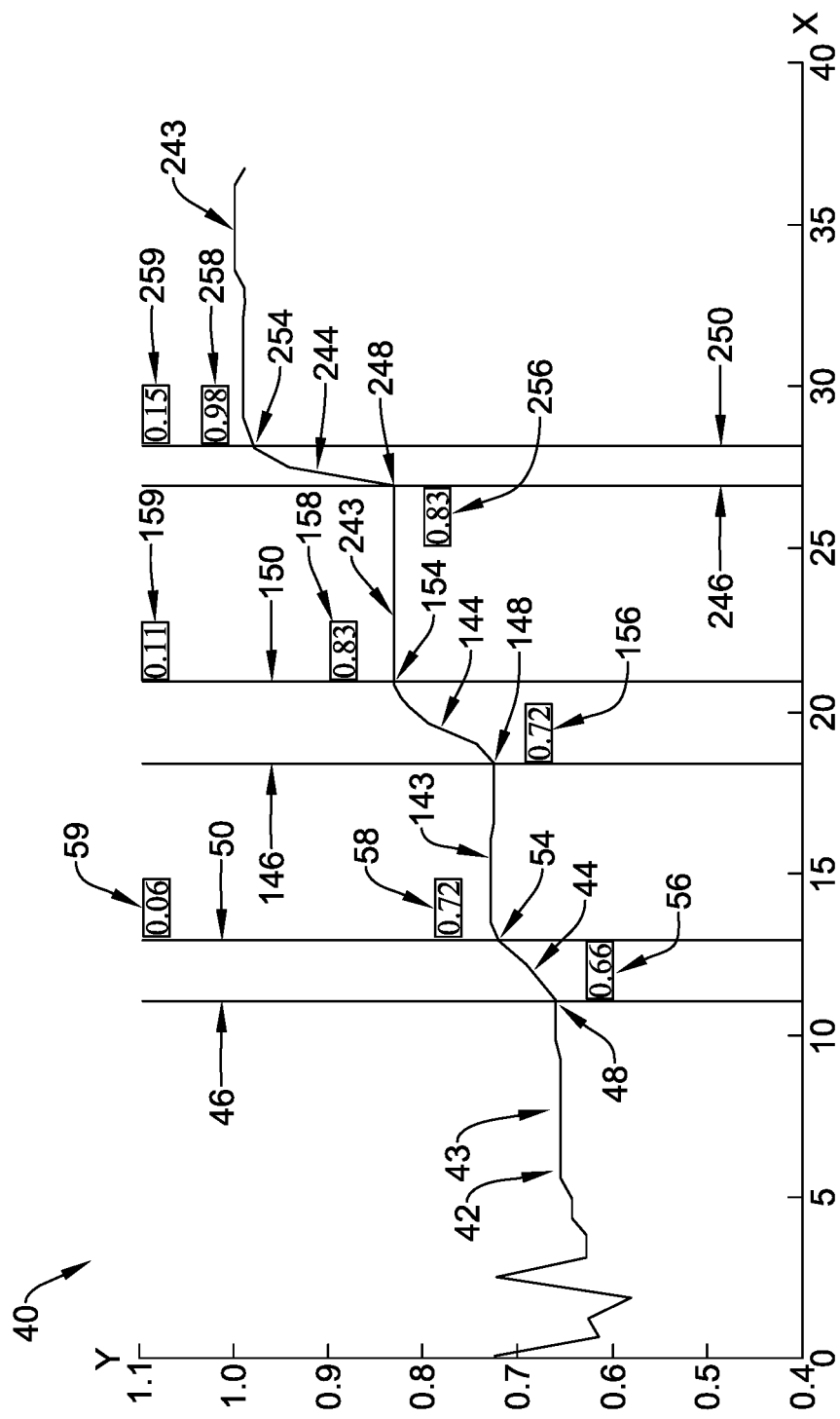
FIG. 3 graphically illustrates and example blood pressure ratio curve showing pressure ratio values over time measured during an example pullback procedure.

Reference is now made to FIG. 3 for a discussion of a prophetic example embodiment of a method for evaluating the vessel of a patient using a system configured to carry out the method, in accordance with this disclosure. FIG. 3 is a schematic drawing of a graph 40 showing a pressure ratio curve 42 that may, for example, be calculated/generated by the processor 88 and output to the display 90. The pressure ratio curve 42 may be generated using and/or in conjunction with methods and systems as disclosed herein. In particular, the method may include obtaining a first series of pressure measurements from a first instrument 10 within the vessel over a time period while the first instrument 10 is moved longitudinally through the vessel from a first position to a second position; and obtaining a second series of pressure measurements from a second instrument 74 positioned within the vessel over the time period while the second instrument remains in a fixed longitudinal position within the vessel. The method may further include calculating a series of pressure ratio values using the first pressure measurements and the second pressure measurements; and generating the pressure ratio curve 42 using the series of pressure ratio values. The method may then entail identifying one or more stepped change in the pressure ratio curve using the ASD process, as discussed above. The system can include a processor, e.g. processor 88, configured and/or programed to carry out the method, including the ASD process. In this particular example, the pressure ratio curve 42 may be generated using FFR pressure ratio values obtained from pressure measurements made during a pullback. The graph 40 shows the pressure ratio curve 42 such that the pressure ratio values ($P_d$/Pa) are represented on the Y axis, and time is represented along the x axis. The curve 42 represents the pressure ratio values along the vessel during the pullback, with the zero time point along the x axis representing the pressure ratio value calculated using $P_d$ pressure measurement obtained from the first instrument 10 at its distal most location during the pullback (e.g. distal of the area of interest), with the right end of the curve 42 along the x axis representing the pressure ratio values calculated using $P_d$ pressure measurement obtained from the first instrument 10 at its proximal most location during the pullback (e.g. at a coronary ostium), with the remainder of the curve 42 between these two end points representing pressure ratio values there between along the vessel.

As shown in FIG. 3, the example pressure ratio curve 42 may include one or more stepped changes (e.g. 44, 144, 244) in the pressure ratio curve, where the stepped changes in the pressure ratio are more significant or rapid within a certain window (e.g. above a certain threshold change), as compared to one or more non-stepped regions (e.g. 43, 143, 243) along the pressure ratio curve 42, where the change in the pressure ratio values within a certain window are less significant, or more gradual (e.g. below a certain threshold change). The processor 88 may use the ASD process and/or algorithm, as described above, to identify the location of the stepped changes (e.g. 44, 144, 244), and optionally label them as desired.

For example, the processor 88 may use the ASD process to identify the stepped change 44 in the pressure ratio curve 42 and optimize the location of a starting point 48 and/or ending point 54 of the stepped change 44 in the pressure ratio curve 42. The processor 88 may also then identify and output to the display marks and/or labels for the identified starting point 48 and ending point 54. For example, the starting point may be marked with a line 46, and the pressure ratio value at the starting point may be shown in a label 56. Similarly, the ending point 54 may be marked with a line 50, and the pressure ratio value at the ending point 54 may be shown in a label 58. Further, a label 59 may also be generated showing the size, amplitude and/or magnitude of the stepped increase (e.g. the difference between the pressure ratio value at the ending point 54 and the starting point 48). For example, as seen in FIG. 3, in the case of the stepped increase 44, the pressure ratio value at the starting point 48 is 0.66, as shown by label 56, and the pressure ratio value at the ending point 54 is 0.72, as shown by label 58. The amplitude of the stepped increase 44 is therefore 0.72−0.66=0.06, which is shown in label 59.

Similarly, the processor 88 may also use the ASD process to identify one or more additional stepped changes (e.g. 144 and 244) in the pressure ratio curve 42, and may optimize the location of starting points (e.g. 148 and 248) and ending points (e.g. 154 and 254) of the one or more other stepped changes 144 and 244 in the pressure ratio curve 42. Similarly, the processor 88 may also then identify and output to the display marks and/or labels for the starting points (e.g. 148 and 248) and ending point (e.g. 154 and 254). For example, the starting points 148 and 248 may be marked with lines 146 and 246, respectively, and the pressure ratio value at each starting point 148 and 248 may be shown in labels 156 and 256, respectively. Similarly, the ending points 154 and 254 may be marked with lines 150 and 250, and the pressure ratio value at each ending point 154 and 254 may be shown in labels 158 and 258, respectively. Further, labels 159 and 259 may also be generated showing the size, amplitude and/or magnitude of the stepped increases (e.g. the difference between the pressure ratio value at the ending point and the starting point of each stepped increase). For example, as seen in FIG. 3, in the case of the stepped increase 144, the pressure ratio value at the starting point 148 is 0.72, as shown by label 156, and the pressure ratio value at the ending point 154 is 0.83, as shown by label 158. The amplitude of the stepped increase 144 is therefore 0.83−0.72=0.11, which is shown in label 159. As also seen in FIG. 3, in the case of the stepped increase 244, the pressure ratio value at the starting point 248 is 0.83, as shown by label 256, and the pressure ratio value at the ending point 254 is 0.98, as shown by label 258. The amplitude of the stepped increase 244 is therefore 0.98−0.83=0.15, which is shown in label 259.

In this particular example, there are significant changes in the pressure ratio value of the curve along the length thereof, including the three stepped changes 44, 144, 244 identified during the pullback using the ADS process. This would indicate three focal lesions within this portion of the blood vessel. The ADS process is able to identify, and optimize the location of, and provide marked starting and ending points of these stepped changes, and indicate the amplitude of each. Thus, the system and method may provide medical personnel useful information about the particular area under examination in determining if interventional treatment is necessary or warranted, and/or how and what kind of treatment to use. For example, the regions of the stepped changes 44, 144, 244 may indicate locations within the vessel potentially worthy of more aggressive invasive treatments, such as angioplasty or stenting, while the non-stepped regions (e.g. 43, 143, 243) may indicate locations within the vessel potentially worthy of less aggressive or less invasive treatments, such as drug therapy or no treatment at all. Additionally, the regions of stepped changes (e.g. 44, 144, 244) may be compared with one another, so that medical personnel may focus treatment on the regions that may have the most significant hemodynamic impact. For example, in this particular case, the most significant stenosed area or lesion appears to be the most proximal one, with the stepped increase 244 measuring 0.15 in amplitude.

Figure 4:
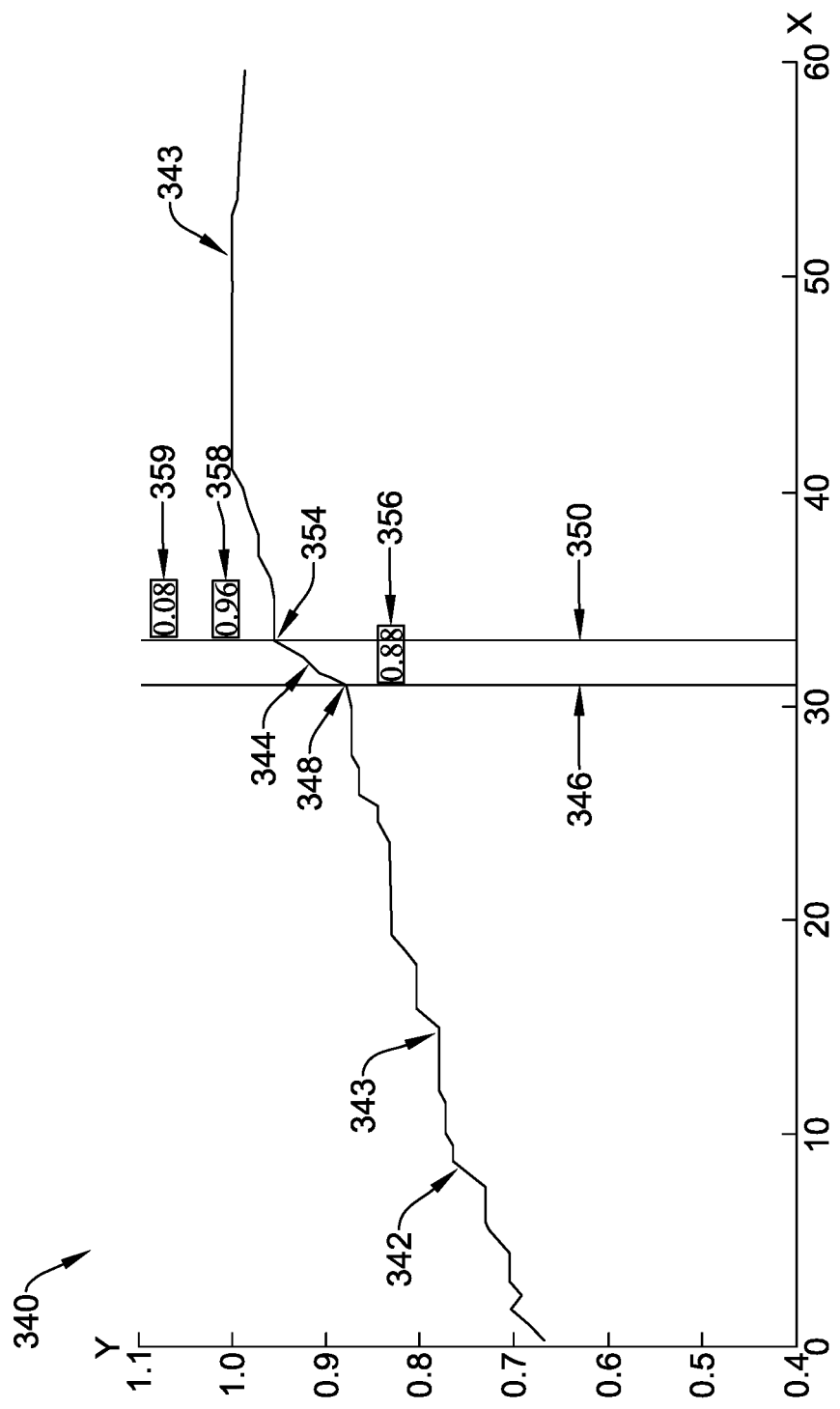
FIG. 4 graphically illustrates another example blood pressure ratio curve showing pressure ratio values over time measured during another example pullback procedure.

Reference is now made to FIG. 4 for discussion of another prophetic example embodiment. FIG. 4 is a schematic drawing of a graph 340 showing a pressure ratio curve 342 that may, for example, be calculated/generated by the processor 88 and output to the display 90. The pressure ratio curve 42 may be generated using and/or in conjunction with methods and systems as disclosed herein, including the use of the ASD process. As shown in FIG. 4, the example pressure ratio curve 342 may include large regions of non-stepped portions 343, where the changes in the pressure ratio values are more gradual and/or less rapid, and only one stepped change 344 in the pressure ratio curve 342, where the changes in the pressure ratio are more significant or rapid within a certain window (e.g. above a certain threshold change). The processor 88 may use the ASD process and/or algorithm, as described above, to identify the location of the stepped change 344, and optionally label it as desired. For example, the processor 88 may use the ASD process to identify the stepped change 344 in the pressure ratio curve 342 and optimize the location of a starting point 348 and/or ending point 354 of the stepped change 344. The processor 88 may also then identify and output to the display marks and/or labels for the identified starting point 348 and ending point 354. For example, the starting point may be marked with a line 346, and the pressure ratio value at the starting point may be shown in a label 356. Similarly, the ending point 354 may be marked with a line 350, and the pressure ratio value at the ending point 354 may be shown in a label 358. Further, a label 359 may also be generated showing the size, amplitude and/or magnitude of the stepped increase (e.g. the difference between the pressure ratio value at the ending point 354 and the starting point 348). For example, as seen in FIG. 4, in the case of the stepped increase 344, the pressure ratio value at the starting point 348 is 0.88, as shown by label 356, and the pressure ratio value at the ending point 354 is 0.96, as shown by label 358. The amplitude of the stepped increase 344 is therefore 0.96−0.88=0.08, which is shown in label 359.

In this prophetic example, the pressure ratio curve 342 is in general more gradual over the majority of the length thereof as compared to the pressure ratio curve 242 discussed above. While there is a significant change in the overall pressure ratio value along the entire length of the curve 342, large portions of the curve 342 are more gradual and/or do not include stepped increases, and only one small stepped change 344 is identified using the ASD process. This may provide medical personnel useful information when determining how to treat this case. Because there is only one small stepped change 344 measuring only 0.08 in amplitude, certain treatments may not be appropriate. For example, removing the more proximal stepped increase 344 by stenting and/or angioplasty may not be sufficient to bring the pressure ratio value along this section back to acceptable levels. As such, due to the diffuse nature of this stenosed area, other treatments, such as bypass surgery may be more appropriate.

Figure 5:
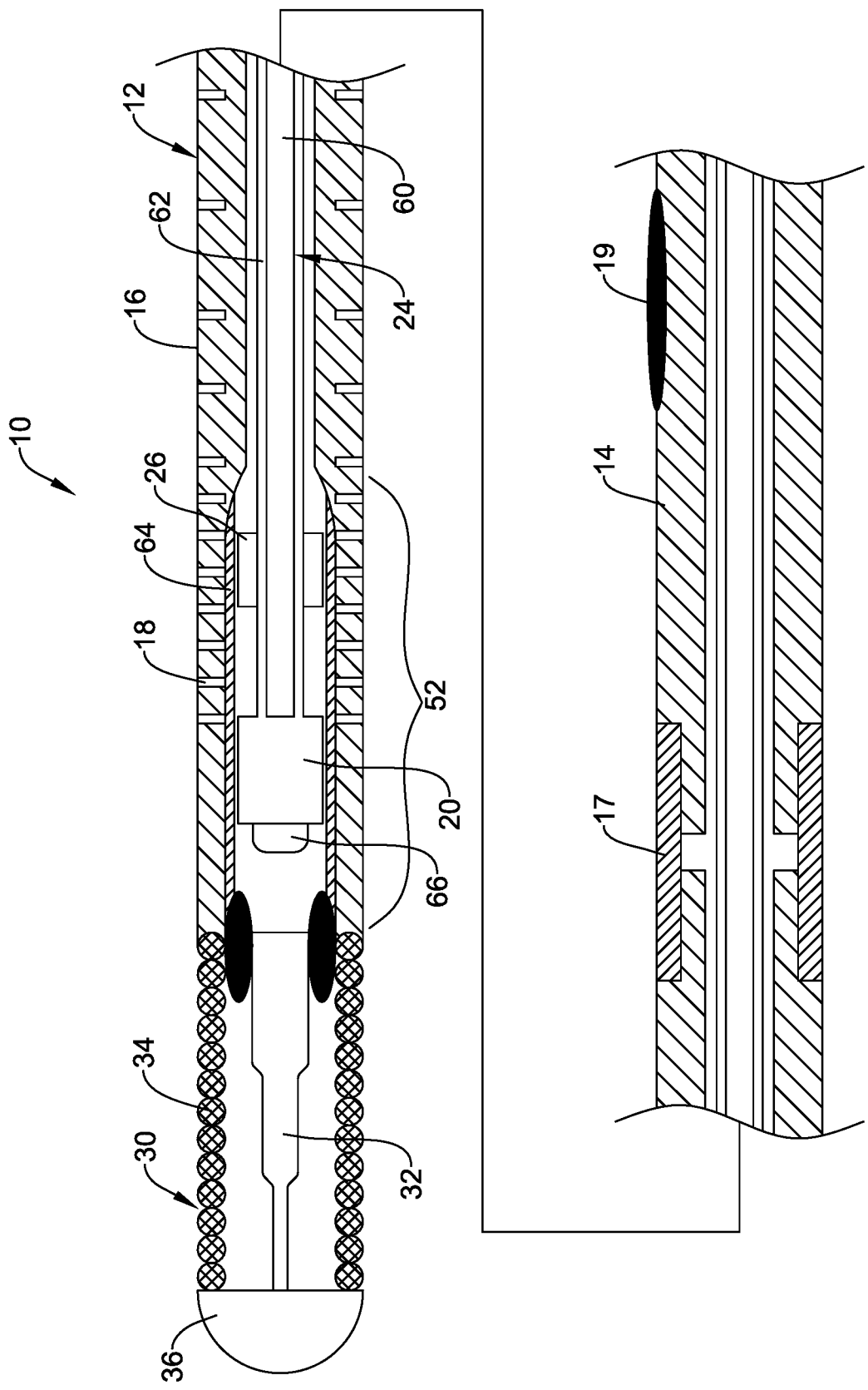
FIG. 5 is a partial cross-sectional side view of a portion of an example medical device.

FIG. 5 shows one example embodiment of a blood pressure sensing guidewire 10 that may be sued, for example, as the first pressure sensing medical device 10. The guidewire 10 may include a shaft or tubular member 12. The tubular member 12 may include a proximal region 14 and a distal region 16. The materials for the proximal region 14 and the distal region 16 may vary and may include those materials disclosed herein. For example, the distal region 16 may include a nickel-cobalt-chromium-molybdenum alloy (e.g., MP35-N). The proximal region 14 may be made from the same material as the distal region 16 or a different material such as stainless steel. These are just examples. Other materials are contemplated.

In some embodiments, the proximal region 14 and the distal region 16 are formed from the same monolith of material. In other words, the proximal region 14 and the distal region 16 are portions of the same tube defining the tubular member 12. In other embodiments, the proximal region 14 and the distal region 16 are separate tubular members that are joined together. For example, a section of the outer surface of the portions 14/16 may be removed and a sleeve 17 may be disposed over the removed sections to join the regions 14/16. Alternatively, the sleeve 17 may be simply disposed over the regions 14/16. Other bonds may also be used including welds, thermal bonds, adhesive bonds, or the like. If utilized, the sleeve 17 used to join the proximal region 14 with the distal region 16 may include a material that desirably bonds with both the proximal region 14 and the distal region 16. For example, the sleeve 17 may include a nickel-chromium-molybdenum alloy (e.g., INCONEL).

A plurality of slots 18 may be formed in the tubular member 12. In at least some embodiments, the slots 18 are formed in the distal region 16. In at least some embodiments, the proximal region 14 lacks slots 18. However, the proximal region 14 may include slots 18. The slots 18 may be desirable for a number of reasons. For example, the slots 18 may provide a desirable level of flexibility to the tubular member 12 (e.g., along the distal region 16) while also allowing suitable transmission of torque. The slots 18 may be arranged/distributed along the distal region 16 in a suitable manner. For example, the slots 18 may be arranged as opposing pairs of slots 18 that are distributed along the length of the distal region 16. In some embodiments, adjacent pairs of slots 18 may have a substantially constant spacing relative to one another. Alternatively, the spacing between adjacent pairs may vary. For example, more distal regions of the distal region 16 may have a decreased spacing (and/or increased slot density), which may provide increased flexibility. In other embodiments, more distal regions of the distal region 16 may have an increased spacing (and/or decreased slot density). These are just examples. Other arrangements are contemplated.

A pressure sensor 20 may be disposed within the tubular member 12 (e.g., within a lumen of tubular member 12). While the pressure sensor 20 is shown schematically in FIG. 3, it can be appreciated that the structural form and/or type of the pressure sensor 20 may vary. For example, the pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, the pressure sensor 20 may include an optical pressure sensor. In at least some of these embodiments, an optical fiber or fiber optic cable 24 (e.g., a multimode fiber optic) may be attached to the pressure sensor 20 and may extend proximally therefrom. The optical fiber 24 may include a central core 60 and an outer cladding 62. In some instances, a sealing member (not shown) may attach the optical fiber 24 to the tubular member 12. Such an attachment member may be circumferentially disposed about and attached to the optical fiber 24 and may be secured to the inner surface of the tubular member 12 (e.g., the distal region 16). In addition, a centering member 26 may also be bonded to the optical fiber 24. In at least some embodiments, the centering member 26 is proximally spaced from the pressure sensor 20. Other arrangements are contemplated. The centering member 26 may help reduce forces that may be exposed to the pressure sensor 20 during navigation of guidewire and/or during use.

In at least some embodiments, the distal region 16 may include a region with a thinned wall and/or an increased inner diameter that defines a sensor housing region 52. In general, the sensor housing region 52 is the region of distal region 16 that ultimately "houses" the pressure sensor 20. By virtue of having a portion of the inner wall of the tubular member 12 being removed at the sensor housing region 52, additional space may be created or otherwise defined that can accommodate the sensor 20. The sensor housing region 52 may include one or more openings such as one or more distal porthole openings 66 that provide fluid access to the pressure sensor 20.

A tip member 30 may be coupled to the distal region 16. The tip member 30 may include a core member 32 and a spring or coil member 34. A distal tip 36 may be attached to the core member 32 and/or the spring 34. In at least some embodiments, the distal tip 36 may take the form of a solder ball tip. The tip member 30 may be joined to the distal region 16 of the tubular member 12 with a bonding member 46 such as a weld.

The tubular member 12 may include an outer coating 19. In some embodiments, the coating 19 may extend along substantially the full length of the tubular member 12. In other embodiments, one or more discrete sections of the tubular member 12 may include the coating 19. The coating 19 may be a hydrophobic coating, a hydrophilic coating, or the like. The tubular member 12 may also include an inner coating 64 (e.g., a hydrophobic coating, a hydrophilic coating, or the like) disposed along an inner surface thereof. For example, the hydrophilic coating 64 may be disposed along the inner surface of the housing region 52. In some of these and in other instances, the core member 32 may include a coating (e.g., a hydrophilic coating). For example, a proximal end region and/or a proximal end of the core member 32 may include the coating. In some of these and in other instances, the pressure sensor 20 may also include a coating (e.g., a hydrophilic coating).

The materials that can be used for the various components of the system 100 and/or the guidewire 10 may include those commonly associated with medical devices. For simplicity purposes, the following discussion makes reference to the tubular member 12 and other components of the guidewire 10. However, this is not intended to limit the devices and methods described herein, as the discussion may be applied to other tubular members and/or components of tubular members or devices disclosed herein.

The tubular member 12 and/or other components of the guidewire 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of guidewire 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guidewire 10 to achieve the same result.

In some embodiments, a degree of Magnetic Resonance Imaging (MRI) compatibility is imparted into the guidewire 10. For example, the guidewire 10, or portions thereof, may be made of a material that does not substantially distort the image and create substantial artifacts (e.g., gaps in the image). Certain ferromagnetic materials, for example, may not be suitable because they may create artifacts in an MRI image. The guidewire 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A system for evaluating a vessel of a patient, the system comprising:
    a display; and
    a processor in communication with the display, the processor configured to:
        obtain a first series of pressure measurements from a first instrument within the vessel over a time period;
        obtain a second series of pressure measurements from a second instrument positioned within the vessel over the time period, wherein the first and second series of pressure measurements are taken at different locations within the vessel;
        calculate a series of pressure ratio values using the first series of pressure measurements and the second series of pressure measurements;
        generate a pressure ratio curve using the series of pressure ratio values;
        output a visual representation of the pressure ratio curve to the display; and
        identify a stepped change in the pressure ratio curve using an automatic step detection process, wherein the automatic step detection process includes:
            identifying a general position of a starting point of the stepped change within a first window along the pressure ratio curve;
            identifying an optimized position of the starting point of the stepped change within a second window along the pressure ratio curve, wherein the second window includes the general position of the starting point; and
            identifying locations within the vessel for treatment corresponding with regions of the stepped change.

2. The system of claim 1, wherein identifying the general position of the starting point of the stepped change includes identifying a change in pressure ratio values within the first window that is at or above a first threshold change value.

3. The system of claim 2, wherein the first window has a predetermined duration along the pressure ratio curve.

4. The system of claim 2, wherein identifying the optimized position of the starting point includes identifying a change in the pressure ratio values within the second window that is above a second threshold change value, wherein the second window is smaller than the first window, and the second threshold change value is smaller than the first threshold change value.

5. The system of claim 4, wherein the second window has a predetermined duration along the pressure ratio curve.

6. The system of claim 5, wherein the predetermined duration of the second window contains a portion of the pressure ratio curve that contains the general position of the starting point of the stepped change.

7. The system of claim 4, wherein the automatic step detection process further includes identifying a general position of an ending point of the stepped change by identifying a change in the pressure ratio values within a third window along the pressure ratio curve that is below a third threshold change value.

8. The system of claim 7, wherein the automatic step detection process further includes identifying an optimized position of the ending point along the pressure ratio curve by identifying a change in the pressure ratio values within a fourth window along the pressure ratio curve that is below a fourth threshold change value, wherein the fourth window is smaller than the third window, and the fourth threshold change value is smaller than the third threshold change value.

9. The system of claim 8, wherein the processor is configured to output to the display a starting point indicator at the optimized position of the starting point, an ending point indicator at the optimized position of the ending point, and a step amplitude label showing a difference between the starting point and the ending point.

10. The system of claim 8, wherein the second and fourth threshold change values are the same in magnitude, wherein the second and fourth windows are the same in duration, or both the second and fourth threshold change values are the same in magnitude and the second and fourth windows are the same in duration.

11. The system of claim 7, wherein the first and third threshold change values are the same in magnitude, wherein the first and third windows are the same in duration, or both the first and third threshold change values are the same in magnitude and the first and third windows are the same in duration.

12. The system of claim 2, wherein the first threshold change value has a magnitude in a range of 0.01 to 0.05.

13. The system of claim 2, wherein the first window is in a range of 3 to 6 heartbeats, wherein the second window is in a range of about 1 to 3 heartbeats, or both the first window is in a range of 3 to 6 heartbeats and the second window is in a range of about 1 to 3 heartbeats.

14. The system of claim 1, wherein the first series of pressure measurements includes a measurement of a distal pressure, and the second series of pressure measurements includes a measurement of a proximal pressure.

15. The system of claim 14, wherein the distal pressure and the proximal pressure are obtained while at least one of the first and second instruments is moved longitudinally through the vessel.

16. The system of claim 1, wherein the stepped change is a stepped increase in the pressure ratio curve.

17. The system of claim 1, wherein the processor automatically identifies one or more additional stepped changes in the pressure ratio curve using the automatic step detection process.

18. A system for evaluating a vessel of a patient, the system comprising:
a display; and
a processor in communication with the display, the processor configured to:
obtain a first series of pressure measurements from a first instrument within the vessel over a time period;
obtain a second series of pressure measurements from a second instrument positioned within the vessel over the time period, wherein the first and second series of pressure measurements are taken at different locations within the vessel;
calculate a series of pressure ratio values using the first series of pressure measurements and the second series of pressure measurements;
generate a pressure ratio curve using the series of pressure ratio values, and output the pressure ratio curve to the display;
identify a stepped change in the pressure ratio curve using an automatic step detection process, wherein the automatic step detection process includes:
identifying a general position of a starting point of the stepped change within a first window along the pressure ratio curve;
identifying an optimized position of the starting point of the stepped change within a second window along the pressure ratio curve, wherein the second window includes the general position of the starting point;
identifying a general position of an ending point of the stepped change within a third window along the pressure ratio curve; and
identifying an optimized position of the ending point of the stepped change within a fourth window along the pressure ratio curve, wherein the fourth window includes the general position of the ending point;
output to the display marks on the pressure ratio curve indicating a location of the starting point and the ending point of the stepped change in the pressure ratio curve; and
identify locations within the vessel for treatment corresponding with regions of the stepped change.

19. The system of claim 18, wherein the processor is configured to automatically identify additional stepped increases in the pressure ratio curve using the automatic step detection process.

20. A method of evaluating a vessel of a patient, the method comprising:
obtaining a first series of pressure measurements from a first instrument within the vessel over a time period;
obtaining a second series of pressure measurements from a second instrument positioned within the vessel over the time period, wherein the first and second series of pressure measurements are taken at different locations within the vessel;
calculating a series of pressure ratio values using the first series of pressure measurements and the second series of pressure measurements;
generating a pressure ratio curve using the series of pressure ratio values;
outputting a visual representation of the pressure ratio curve to a display; and
identifying a stepped change in the pressure ratio curve using an automatic step detection process, wherein the automatic step detection process includes:
identifying a general position of a starting point of the stepped change within a first window along the pressure ratio curve;
identifying an optimized position of the starting point within a second window along the pressure ratio curve, wherein the second window includes the general position of the starting point; and
identifying locations within the vessel for treatment corresponding with regions of the stepped change.

* * * * *